United States Patent [19]

Thomas-Leurquin et al.

[11] Patent Number: 4,789,662

[45] Date of Patent: Dec. 6, 1988

[54] METHOD FOR THE TREATMENT OF PERIODONTAL POCKETS WITH A COMPOSITION COMPRISING COLLAGEN AND AN ANTISEPTIC OR ANTI-INFLAMMATORY SUBSTANCE

[75] Inventors: Geneviève Thomas-Leurquin; Anne Gayot, both of Lille Cedex; Pierre Poitou; Serge Basquin, both of Castres, all of France

[73] Assignee: Pierre Fabre Medicament, Paris, France

[21] Appl. No.: 944,541

[22] Filed: Dec. 19, 1986

[30] Foreign Application Priority Data

Dec. 23, 1985 [FR] France .................. 85 19035

[51] Int. Cl.$^4$ .................. A61K 37/02; A61K 31/155
[52] U.S. Cl. .................. 514/21; 514/801; 523/115; 128/DIG. 8; 424/405; 424/422; 424/489
[58] Field of Search .................. 530/356; 514/21, 801; 523/115; 128/DIG. 8; 424/405, 422, 491, 489

[56] References Cited

U.S. PATENT DOCUMENTS

| | | | |
|---|---|---|---|
| 3,435,117 | 3/1969 | Nichols | 424/271 |
| 3,821,371 | 6/1974 | Battista | 424/145 |
| 4,291,013 | 9/1981 | Wahlig et al. | 424/95 |
| 4,517,173 | 5/1985 | Kizawa et al. | 424/435 |
| 4,572,832 | 2/1986 | Kigasawa et al. | 514/773 |

FOREIGN PATENT DOCUMENTS 2131293 6/1984 United Kingdom .

OTHER PUBLICATIONS

Chemical Abstracts, 107(6): 46227k, Leurquin-Thomas et al., "Preparation of Collagen-Based Implants", 1986.

*Primary Examiner*—John Kight
*Assistant Examiner*—Nathan M. Nutter
*Attorney, Agent, or Firm*—Dressler, Goldsmith, Shore, Sutker & Milnamow, Ltd.

[57] ABSTRACT

The present invention relates to a composition consisting of an association of collagen with an antiseptic and/or antiinflammatory active principle, the process for its preparation and its use for the production of a pharmaceutical composition.

The pharmaceutical composition according to the invention comprises collagen as the vehicle and at least one antiseptic and/or inflammatory substance as the active principle.

Application to the topical treatment of periodontal complaints.

10 Claims, No Drawings

METHOD FOR THE TREATMENT OF PERIODONTAL POCKETS WITH A COMPOSITION COMPRISING COLLAGEN AND AN ANTISEPTIC OR ANTI-INFLAMMATORY SUBSTANCE

The present invention relates to a novel solid therapeutic composition consisting of an association of collagen with an antiseptic and/or antiinflammatory active principle, for the treatment of periodontal diseases, in particular for the treatment of deep or superficial periodontal pockets.

The periodontium is the group of tissues which support the teeth. It is formed by the gingiva and, in its deep part, by the alveolar bone, the cementum and the periodontal ligament. The latter is a group of alveolodental ligaments which hold the tooth firmly in the alveolar site.

At the tooth-gingiva junction, there is a space of about 1 mm in depth—the gingivodental crevice—which is closed by the junctional epithelium. This epithelial attachment is a real barrier between the external and internal environments.

The periodontal pocket, which is a consequence of periodontitis, can be described as the result of an abnormal increase in the depth of the gingivodental crevice with apical migration of the junctional epithelium, following successive inflammatory reactions which lead to degeneration of the connective tissues constituting the deep periodontal structures.

The main etiological factor involved in periodontal disease is recognized to be of bacterial origin and associated with dental plaque.

The failure to exercise buccodental hygiene results in an accumulation of plaque at the tooth-gingiva junction and in the gaps between the teeth. An increase in volume of the plaque leads to gingivitis, which most frequently develops into periodontitis.

The inflammation spreads along the root. The transition from gingivitis to periodontitis is accomplished by a change in the constitution of the bacterial flora of the dental plaque The treatment of periodontal pockets consists in removing the local irritants, including the subgingival dental plaque, and in restoringthe architecture of the bone and gingiva so as to make the periodontium functional once again The introduction of an antibacterial active principle into the periodontal pocket affords effective control of the development of the subgingival dental plaque. The means used in the case of more or less superficial periodontal pockets are as follows:

daily irrigation of the periodontal pockets with a solution of the active principle, and the introduction into the periodontal pocket of a hollow fiber or a polymer film containing the active principle and ensuring a sustained release of the active principle (a few hours to a few days) into the pocket.

Although effective from the bacteriological and clinical point of view, these means nevertheless have the following disadvantages:

irrigation involves skill and cooperation on the part of the patient, and polymer films and hollow fibers are not absorbable and have to be removed from the pocket after the active principle has been released, which is likely to injure the tissues.

In the case of more serious complaints, restoration of the periodontium most often requires surgical techniques to remove the defective tissues and reposition the remaining tissues.

In some cases, fillers are introduced into the lesions below the bone. The choice of materials is based on their possible induction of osteogenesis or tissue regeneration.

These products are disadvantaged by their preparation, storage and handling

Thus, there is no composition at the present time which is capable either of treating superficial periodontal pockets without injuring the tissues, or of treating deeper periodontal pockets which require a surgical intervention as well.

It is known furthermore that the alveolodental ligaments, the junctional epithelium and, more generally, the group of tissues making up the periodontium consist largely of collagen.

Collagen is a glycoprotein representing about 40% of the proteins in an adult organism. By virtue of its triple helix structure and because of the large number of hydrogen and Van der Waals bonds joining its component amino acids together, collagen is very stable and hence provides the connective tissues with remarkable mechanical properties. It is also involved in the healing process, on the one hand by promoting hemostasis since it induces adhesion and platelet aggregation, and on the other hand by taking part in the production of a granulation tissue in which cells such as fibroblasts come to develop, thereby permitting tissue regeneration. Moreover, like the majority of substances which make up the organism, collagen is continuously renewed.

The metabolism of collagen varies with age and from one tissue to another. In the periodontal ligaments, it is 5 days, i.e. 15 times faster than in the dermis.

Furthermore, exogenous collagen (for example collagen of bovine origin) will be metabolized in the same way as endogenous collagen when introduced into the organism. This material is therefore perfectly absorbable. For example, the average absorption time of a non-denatured native collagen used as a hemostatic agent is 3 weeks. The absorption time of collagen can be extended by increasing its degree of crosslinking.

In addition, compared with other proteins, collagen is weakly immunogenic and, for example, some of the antigenic determinants carried by human collagen are 95% superimposable on those carried by a collagen of bovine origin.

The stability of collagen, its ability to accelerate tissue regeneration, its absorbability and its tolerance by the organism give this macromolecule properties of biocompatibility which make it a preferred active principle vehicle and support for uses involving intimate and prolonged contact with wounded living tissues.

It is for this reason that the present invention proposes a solid pharmaceutical composition for introduction into periodontal pockets in order to treat them, which comprises collagen as the vehicle and at least one antiseptic and/or antiinflammatory substance as the active principle.

This association has very substantial advantages.

It is advantageous to introduce collagen into the lesions below the bone because this collagen provides a stroma for cell proliferation and with it the possibility of tissue regeneration after differentiation of the mesenchymal cells. The addition of an antibacterial active principle can temporarily ensure that the operating site is aseptic and reduce an unduly rapid degradation of the material due to a substantial afflux of cells to defend the organism, caused by the inflammation. A variety of substances, such as metronidazole or chlorhexidine, can be used as the antibacterial active principle.

According to the present invention, the pharmaceutical composition preferably contains, as the active principle, chlorhexidine or one of its salts selected in particular from the group comprising the diacetate, the digluconate and the dihydrochloride, because this active principle has antiinflammatory properties in addition to its antibacterial properties.

Chlorhexidine is a molecule of basic character which has a broad spectrum of antibacterial activity against Gram+ and Gram− bacteria.

In vivo, it possesses a good antiplaque activity which persists with time. This residual activity is due to the adsorption properties of chlorhexidine on the hydroxyapatite of the tooth and to its interactions with the compounds in the saliva, such as the proteins and mucins. Once adsorbed in this way, the chlorhexidine prevents the tooth surfaces and the mucosa from being colonized by the bacteria. It is gradually released into the environment, where it still exerts an antibacterial activity.

In contrast to antibiotics, chlorhexidine does not induce bacterial resistance and does not lead to allergic manifestations in the patients. Chlorhexidine has a very low toxicity since this active principle is not absorbed into the blood.

Association of this substance with collagen makes it possible to obtain a well-defined local therapeutic activity which is spatially restricted to the site of application and can be modified with time.

This association is preferably made up with a weight ratio collagen/chlorhexidine of between 1 and 3. The preferred embodiment of the composition according to the invention uses a weight ratio collagen/chlorhexidine which is approximately equal to 2.

The pharmaceutical form which is to be introduced into the periodontal pockets in order to control the subgingival plaque or to fill the periodontal lesions below the bone must advantageously satisfy certain criteria:

the form must be sterile since it is intended for implantation;

the form must be flexible so as not to cause irritation or discomfort;

the form must be adaptable to different volumes since the size and configuration of the pockets are variable; and the form must be easy to handle.

These criteria can be satisfied by a variety of pharmaceutical forms. Preferably, the composition according to the present invention is in the form of films or lyophilizates. The films are preferably in the form of small flexible and strong leaves with an average thickness of about 120 μm. The lyophilizates are preferably in the form of pellets, which are also flexible and compressible.

The use of films and lyophilizates can be combined with a surgical intervention, in which case the form is applied to the desired location by the practitioner. The forms can be used after cleansing of the periodontal pockets, without surgery, in which case they are introduced into the lesion by the practitioner using suitable instruments. Their purpose here is to control the development of the subgingival bacterial plaque.

These films or lyophilizates are most commonly intended to be used in the form of implants.

These forms are defined as implants, irrespective of their use, i.e. whether or not they are combined with a surgical intervention, because they are in prolonged contact with living tissues which are not subjected to the external conditions when they are in a normal state of health.

Whatever its form, the pharmaceutical composition according to the present invention has an active principle concentration of between 0.5 mg and 5 mg per unit dose. This concentration is preferably about 2.5 mg.

The collagen used in the composition according to the present invention is preferably non-decrosslinked collagen of bovine origin.

The present invention also relates to a process for the preparation of the said pharmaceutical composition, which comprises the following three steps:

(a) the collagen is solubilized in acetic acid until a solution with a collagen concentration of between 0.5 g and 1.5 g per 100 g of solution is obtained;

(b) the active principle is solubilized in distilled water until a solution with an active principle concentration of between 1 g and 2 g per 100 g of solution is obtained; and (c) the two solutions obtained after steps (a) and (b) are mixed together and the solvents are then removed.

The mixture obtained after step (c) is for example poured into a flat-bottomed container in order to allow the solvent to evaporate and a film to form, or alternatively divided up into flasks, frozen and lyophilized.

Finally, the present invention relates to the use of an association of collagen with an active principle, such as chlorhexidine or one of its salts, for the production of a composition for the topical treatment of periodontal complaints.

The technical preparation of the films and lyophilizates will be understood more clearly from the description of the following examples, which are given simply by way of illustration.

1. General points relating to the preparation of films and lyophilizates

These two forms can be obtained as unit doses containing a determined amount of active principle, or in "bulk" form containing a homogeneous distribution of the active principle, all or part of the preparation being used as required.

The active principle concentration of the pharmaceutical form was fixed after studying the antibacterial activity of variable amounts of chlorhexidine present in films, on bacteria isolated from dental plaque.

Culture inhibition was obtained for a chlorhexidine concentration of about 2.5 mg/cm$^2$ in the film.

This was considered to be the optimum concentration for practical purposes and was used for both the films and the lyophilizing. It was shown, however, that a concentration of for example 0.5 mg/cm$^2$ is sufficiently active in vivo in certain cases.

Consequently, the examples described below for the preparation of the films and lyophilizates can be adapted to the preparation of compositions whose unit form has an active principle concentration of between 0.5 mg and 5 mg.

The ratio collagen/chlorhexidine is set at 2/1 by weight. The amounts thus used make it possible to obtain flexible and strong films and lyophilizates.

2. Example of film production

Step 1: Solubilization of the collagen

The collagen used is a non-decrosslinked native collagen of bovine origin, which is in the form of fibers. The fibers are dispersed and solubilized for 2 hours in a 0.1M solution of acetic acid, with magnetic stirring, so that the collagen concentration of the solution is equal to 1% by weight.

Step 2: Addition of the active principle

The amount of chlorhexidine diacetate required to give a collagen/chlorhexidine ratio of 2/1 is weighed out.

The chlorhexidine diacetate is dissolved in a sufficient amount of distilled water for the concentration of the solution to be equal to 1.5% by weight.

The chlorhexidine diacetate solution is added to the collagen solution, magnetic stirring being maintained for about 10 minutes.

Step 3: Preparation of the films

The mixture obtained is poured into a perfectly flat-bottomed container, the area of which is determined so that the chlorhexidine diacetate concentration of the finished product is equal to 2.5 mg/cmhu 2. Thus, for example, sterile Petri dishes with an area of about 55.4 cm$^2$ can be used as containers.

If the mixture obtained after step c) has an overall volume of 40 ml made up of 30 ml of a dispersion of 300 mg of collagen films in 0.1 M acetic acid, to which 150 mg of chlorhexidine acetate previously solubilized in 10 ml of distilled water have been added, the film obtained then has a chlorhexidine content of 2.7 mg/cm$^2$. The container holding the mixture is placed in a ventilated oven at a temperature not exceeding 30° C.

The film is obtained by evaporation of the solvent, the time required for this operation being 2 to 3 days.

The film obtained is weighed. Squares with an area of 1 cm$^2$ are cut out of the film and then weighed and packed individually in glass flasks.

3. Example of lyophilizate production

The production of the lyophilizates is identical to the production of the films as regards steps 1 and 2.

Step 3: Preparation of the lyophilizates

Using a pipette, the mixture obtained is divided up into 5 ml lyophilization flasks. The volume of mixture taken must correspond to an amount of about 2.5 mg of chlorhexidine in the final form. Thus, for example, it is possible to take a volume of about 0.72 ml of the mixture obtained after step c). If this mixture has the same composition as that indicated previously for the preparation of the films, the lyophilizates obtained then have a chlorhexidine content of 2.7 mg per unit dose.

The flasks are subjected to lyophilization, the operation lasting 48 hours.

In a first stage, it consists in freezing the product, which takes 6 h 30 min.
- temperature of the enclosure: −50° C.
- temperature in the core of the product: −45° C.

The second stage is lyophilization, which takes 24 h. freezing is stopped, without heating;
- a moderate vacuum is applied to ensure that the solvent starts evaporating off; and
- a high vacuum is then applied with the temperature being increased to 35° C.

4. Sterilization

The final operation in the production of the films and lyophilizates is sterilization.

An example of the sterilization technique is sterilization with ethylene oxide.

It is carried out under conditions which are such that the products are not degraded, i.e.:
- temperature: 35° C.–40° C.
- humidity: 60%
- pressure slightly below atmospheric pressure
- duration of the operation: 14 h
- composition of the gaseous mixture: air 50%, ethylene oxide 50%. After sterilization, the flasks are capped and the caps crimped on.

5. Quality controls

The quality controls carried out on the films and lyophilizates are satisfactory in terms of the sterility and the residual ethylene oxide content.

The release of the chlorhexidine acetate in vitro was studied on the films and the lyophilizates.

The weighed product is held in a cell kept at a temperature of 37° C. in a temperature-controlled water bath. A liquid is passed through the product at a rate of 0.5 ml/min for 7 hours. The liquid is a solution of dilute electolytes (sic), simulating the saliva, and has the following composition:

| | |
|---|---|
| $CaCl_2$ | 0.6 mM |
| $NaH_2PO_4.2H_2O$ | 1.8 mM |
| $NaHCO_3$ | 12 mM |
| HCl | 1 mM |
| pH | 7.4 |

The liquid is collected for quantitative analysis of the chlorhexidine acetate by Hoolbrook's colorimetric technique.

The results are shown in the tables which follow.

TABLES OF RESULTS
Chlorhexidine acetate released from 7 lyophilizates, expressed in % of the theoretical amount of chlorhexidine acetate

| | Lyophilizate | | | | | | | | Standard |
|---|---|---|---|---|---|---|---|---|---|
| Time | 1 | 2 | 3 | 4 | 5 | 6 | 7 | Mean | deviation |
| 1 h | 26.75 | 47.5 | 40 | 45.4 | 41.4 | 53 | 34 | 41.15 | 8.09 |
| 2 h | 42.3 | 61.8 | 55 | 63 | 62 | 73.4 | 48.7 | 58 | 9.5 |
| 3 h | 50.4 | 68.5 | 64 | 71.8 | 71.3 | 82.7 | 55.5 | 66.3 | 10 |
| 4 h | 58.26 | 72.6 | 70 | 78.4 | 76.8 | 87 | 61.8 | 72.1 | 9.1 |
| 5 h | 63 | 74.3 | 74 | 81 | 80 | 89.8 | 66 | 75.4 | 8.5 |
| 6 h | 64.8 | 75.1 | 75.8 | 82 | 81 | 90.7 | 70 | 77 | 7.8 |
| 7 h | 65.8 | 76.3 | 77.2 | 82.7 | 82 | 91.5 | 73 | 78.3 | 7.5 |

Chlorhexidine acetate released from 4 films, expressed in % of the theoretical amount of chlorhexidine . . . (sic)

| | Film | | | | | Standard |
|---|---|---|---|---|---|---|
| Time | 1 | 2 | 3 | 4 | Mean | deviation |
| 1 h | 48.4 | 46.3 | 50.9 | 67.7 | 53.3 | 8.45 |
| 2 h | 60.5 | 63.3 | 71.6 | 72.1 | 66.8 | 5.07 |
| 3 h | 67.37 | 68.1 | 76 | 74.4 | 71.4 | 3.78 |
| 4 h | 72.7 | 72.1 | 82 | 76 | 75.7 | 3.9 |
| 5 h | 77.8 | 75.5 | 87.5 | 77.1 | 79.4 | 4.7 |
| 6 h | 81 | 77.1 | 89.7 | 78 | 81.45 | 4.9 |

6. Clinical trials

The compositions according to the invention showed an excellent activity in the treatment of periodontal complaints, as evidenced in particular by the clinical study reported below.

The aim of this preliminary clinical study on man was to examine the value of the system described for the treatment of periodontitis, i.e.:
the antibacterial activity of the pharmaceutical form due to the release of the chlorhexidine;
the participation of the collagen in healing and in the restructuring of the periodontium;
the absorbability of the material; and
the tolerance.

Three cases were studied:
two involving the use of the lyophilizate; and
one involving the use of the film.

The three cases are cases of complex periodontitis requiring surgery to cut a flap.

The patients are subjected in the same manner to an initial preparation consisting of scaling and surfacing of the lesions.

The adoption of a plaque control bringing the Oleary index to below 10% and mouthwashes with a pure 0.2% solution of chlorhexidine digluconate for 2 minutes three times a day.

Each case is documented by means of photographs, X-rays, probing of the pockets and records of the plaque index (PII) and inflammation index (GI) at the following different times: 8 days—15 days—3 months—6 months.

EXAMPLE 1

Case no. 1—7-month history 1.1—Treatment and results

Product used: collagen/chlorhexidine lyophilizate
Patient: 40-year-old man
Lesion treated: tooth 26, mesial, distal and palatal type III interradicular lesion With the marginal gingival level held at the enamel-cementum junction, the pockets are 6 to 7 mm deep and a Nabers probe penetrates the furcation from all sides. After initial preparation, the PII and GI indices are zero. The tooth mobility is III.

A curettage flap is cut opposite 26, the incisions being inside the sulcus and no tissue being ejected. The granulation tissue is opened up and the lesion below the bone is prepared. The root surfaces are treated mechanically and chemically with a citric acid solution of pH 1. The collagen/chlorhexidine lyophilizate is placed in the most steeply sloping zone of the bone lesion, after which the flaps are hermetically sutured at the top, above the zone treated in this way. A surgical dressing of the Coë Pack type is placed on the vestibular and palatal sides. Mouthwashes with a pure 0.2% solution of chlorhexidine digluconate for 2 minutes 3 times a day are prescribed.

After 8 days, the sutures are removed and the gingival tissues, free from any inflammatory manifestations, are perfectly adapted to the root surfaces and show no recession. The plaque and inflammation indices are zero. The mobility is slightly greater.

After 15 days, the inflammatory appearance of the gingival tissues persists, a slight gingival recession has been established, the mobility is II+ and the indices have been maintained.

Regular checks up to 7 months after the operation show that the mobility has been reduced to zero and that the results have been maintained. A substantial recession exposes the furcation zone, but each of the 3 roots is perfectly set in the gingival tissues and it is not possible to probe more than 2 mm without causing bleeding. The plaque control care is carried out meticulously.

1.2 —Discussion of case no. 1

This first case, with a seven-month history, demonstrates the perfect tolerance of the collagen/chlorhexidine lyophilizate in the short term and long term.

Compared with cases of this type which have been treated in the conventional way, healing has been accelerated and recession "guided" so that residual pockets do not remain.

The "in situ" collagen, releasing the chlorhexidine, seems to have acted as a healing support, preventing the spread of epithelium down to the bottom of the bone defect. This does not have any connection with the acid treatment of the root surfaces and the care applied to the imperviousness of the sutures.

According to the Melcher domain theory, this material, placed between the root surface and the inside of the flap, has served as a protection, preventing the cells of the gingival connective tissue from coming into direct contact with the root surface which has been rendered biocompatible. This may therefore have favored invasion of the operating site by the cells originating from the periodontal ligament, which, according to work by Lindhe and Karring (1985), are capable of producing a connective attachment, at least over a minimal distance.

EXAMPLE 2

Case no. 2—6-month history 2.1 —Treatment and results

Product used: collagen/chlorhexidine lyophilizate
Patient: 24-year-old man suffering from juvenile periodontitis
Lesion treated: tooth 36 - interradicular lesion below the bone The protocol is the same except for the addition, conventional in cases of juvenile periodontitis, of antibiotherapy (DOXYCLINE (sic) 4 days, 10 days withdrawal, 20 days and resumption) as well as the introduction of synthetic filler into the lesion (2 doses of 1 mg); after the insertion of the absorbable filler, the collagen/chlorhexidine lyophilizate is placed in the interradicular lesion on the lingual side and the flaps are stuck via the inside with Tissucol (human fibrinogen) and then sutured.

The pocket in this site has decreased from 5 mm to 2 mm after 6 months, the mobility of III+ has changed to I and no inflammation or plaque deposit are recorded after 6 months, the patient exercising perfect plaque control and remaining under a plaque inhibitor.

2.2 Discussion of case no. 2

The GT 2 is coupled with the use of "Synthograf" and fibrin adhesive and seems to potentiate both the products.

It is noteworthy that interradicular lesions have the worst prognosis in conventional practice and that this case, like the previous one, showed particularly favorable healing.

EXAMPLE 3

Case no. 3—1-year history

3.1 Treatment

Product used: collagen/chlorhexidine film containing a dose of 0.5 mg/cm$^2$
Patient: 60-year-old woman
Lesion treated: tooth 26 - pockets below the bone The lesion is the center of an intervention of the "esthetic access flap" type, making it possible to treat the periodontal pockets with access to the root surfaces and very hermetic closure of the operating site.

An X-ray in conjunction with probing of the pockets shows the presence of pockets below the bone which are 8 mm in the mesial direction, 5 mm in the vestibular direction and 4 mm in the distal direction; the palatal probe penetrates 3 mm.

The Pbi and SBi have values of zero and the tooth mobility is III (more than 1 mm on either side of the median axis in a vestibulopalatal direction).

The intervention consisted, after the cutting of a vestibular and palatal mucoperiosteal flap, of a curettage of the granulation tissues and a mechanical root preparation with a curette, as well as a chemical preparation of the cementum surfaces by applying a saturated solution of citric acid of pH 1.

Particular care is devoted to opening up the mesiovestibular lesion below the bone, which confirms the existence of a type II mesial interradicular lesion, the probe penetrating the furcation by 2 mm from the mesial side. On the one hand the collagen/chlorhexidine film is applied to the treated vestibular root surface, inside the flap, and on the other hand a fragment thereof is inserted in the interradicular lesion.

After reapplication of the flaps and intimate coaptation of the vestibular and palatal flanks, held by interproximal sutures using vertical mattress stitch (sic), a surgical dressing of the Coë Pack type is applied for 8 days and mouthwashes with a 0.2% solution of chlorhexidine digluconate for 2 minutes 3 times a day are prescribed.

3.2 - Results 8 days after the intervention, the dressing is removed, the "collagen/chlorhexidine film" can be seen in the cervical region and the mucoperiosteum is not hermetically adapted to the root in the vestibular and mesial zones.

No sign of inflammation is detected and a sweep with the probe shows that there is no deposit of bacterial plaque. There is no halitosis. The tooth mobilization is greater.

The patient makes no mention of pain or discomfort.

The sutures are removed, a dressing is not reapplied and the resumption of meticulous hygiene activities is prescribed together with continuation of the chlorhexidine mouthwashes.

15 days after the intervention, the film has disappeared from the lesion, either by absorption or by mechanical removal. Healing with negative architecture is observed at the point where the film was inserted. The site is slightly inflammatory and painful and there is a development of dental plaque.

3 months after the intervention, the negative architecture has disappeared, except in the mesial region. The vestibular flap is perfectly reapplied, but its marginal edge has undergone a 3 mm recession, reducing the depth of the pocket to 2 mm.

The depth of the pocket in the mesial position leading to the furcation zone has been reduced from 8 mm to 6 mm. The mobility has been reduced to II on the ARPA scale.

After 1 year, the mobility of 26 is physiological.

The depth of the pocket in the vestibular position is 2 mm; it remains 4 mm in the mesial position with a defect in the gingival architecture of the papilla. The plaque index (PII) and inflammation index (GI) are zero.

These preliminary clinical studies show the perfect tolerance of the collagen/chlorhexidine lyophilizates used to fill periodontal pockets. The collagen improves the healing of the treated lesions and seems to partake in the establishment of new tissue structures.

The release of chlorhexidine at the implantation site prevents the development of plaque and keeps the lesion aseptic after the operation.

The collagen/chlorhexidine films are of less value when applied to lesions below the bone which require surgery.

They can be reserved for application to periodontal pockets which do not require surgery, in which case they will control the development of dental plaque by the release of chlorhexidine, which will be maintained for at least 8 hours according to the results obtained from release experiments in vitro.

What is claimed is:

1. The method of treating a patient having at least one periodontal pocket which comprises introducing into said pocket a pharmaceutical composition comprising collagen as the vehicle and at least one antiseptic or anti-inflammatory substance as the active principle and maintaining said pharmaceutical composition in said pocket until said collagen is absorbed therefrom, said composite being in a flexible form.

2. A method as claimed in claim 1, wherein the said active principle is selected from the group consisting of chlorhexidine and its salts.

3. The method of claim 2 wherein said active principle is selected from the group consisting of chlorhexidine diacetate, chlorhexidine digluconate and chlorhexidine dihydrochloride.

4. A method as claimed in claim 2, wherein the weight ratio collagen/chlorhexidine is betwene 1:1 and 3:1.

5. A method as claimed in claim 4 in which said composition is in the form of a film.

6. A method as claimed in claim 4, in which said composition is in the form of a lyophilizate.

7. A method as claimed in claim 4, in which said composition is in the form of an implant.

8. A method as claimed in claim 2, in which the active principle concentration is between 0.5 mg and 5 mg per unit dose.

9. A method as claimed in claim 2, wherein the collagen used is a non-decrosslinked native collagen of bovine origin.

10. A method as claimed in 1 wherein said pharmaceutical composition is prepared by the following steps:

(a) the collagen is solubilized in acetic acid until a solution with a collagen concentration of between 0.5 g and 5 per 100 g of solution is obtained;
(b) the active principle is solubilized in distilled water until a solution with an active principle concentration of between 1 g and 2 g per 100 g of solution is obtained; and
(c) the two solutions obtained after steps (a) and (b) are mixed together and the solvents are then removed.

* * * * *

UNITED STATES PATENT AND TRADEMARK OFFICE
CERTIFICATE OF CORRECTION

PATENT NO. : 4,789,662
DATED : December 6, 1988
INVENTOR(S) : Leurquin et al.

It is certified that error appears in the above-identified patent and that said Letters Patent is hereby corrected as shown below:

Col. 1, line 46, "restoringthe" should be --restoring the--.

Col. 5, line 25, "2.5 mg/cmhu 2" should be --2.5 mg/cm$^2$--.

Col. 11, line 3, "5" should be --1.5 g--.

Signed and Sealed this

Third Day of October, 1989

Attest:

DONALD J. QUIGG

Attesting Officer Commissioner of Patents and Trademarks